US010179205B2

(12) United States Patent
Friedrich

(10) Patent No.: US 10,179,205 B2
(45) Date of Patent: Jan. 15, 2019

(54) PASSIVE SAFETY HUBER NEEDLE

(71) Applicant: Novum Vascular, LLC, San Antonio, TX (US)

(72) Inventor: Terrell L. Friedrich, Helotes, TX (US)

(73) Assignee: Novum Vascular, LLC

( * ) Notice: Subject to any disclaimer, the term of this patent is extended or adjusted under 35 U.S.C. 154(b) by 129 days.

(21) Appl. No.: 15/016,206

(22) Filed: Feb. 4, 2016

(65) Prior Publication Data

US 2017/0224917 A1 Aug. 10, 2017

(51) Int. Cl.
*A61M 5/162* (2006.01)
*A61M 25/06* (2006.01)
*A61M 5/32* (2006.01)
*A61M 5/158* (2006.01)
*A61M 39/02* (2006.01)

(52) U.S. Cl.
CPC .......... *A61M 5/1626* (2013.01); *A61M 5/158* (2013.01); *A61M 5/3216* (2013.01); *A61M 5/3219* (2013.01); *A61M 5/3275* (2013.01); *A61M 25/0631* (2013.01); *A61M 25/0637* (2013.01); *A61M 25/0612* (2013.01); *A61M 39/02* (2013.01); *A61M 2005/1581* (2013.01)

(58) Field of Classification Search
CPC .. A61M 5/1626; A61M 5/158; A61M 5/3216; A61M 5/3219; A61M 5/3275
See application file for complete search history.

(56) References Cited

U.S. PATENT DOCUMENTS 4,888,001 A * 12/1989 Schoenberg ...... A61M 25/0637
604/162
6,309,376 B1 * 10/2001 Alesi .................... A61M 5/158
604/263
6,500,154 B1 * 12/2002 Hakky .................. A61M 25/02
604/174

(Continued)

FOREIGN PATENT DOCUMENTS

EP 1256355 A1 11/2002
EP 1415674 A1 5/2004
WO WO-2002/055132 A2 7/2002

*Primary Examiner* — Nathan R Price
*Assistant Examiner* — Dung Ulsh
(74) *Attorney, Agent, or Firm* — Mintz Levin Cohn Ferris Glovsky and Popeo, P.C.

(57) ABSTRACT

A safety needle system includes a safety mechanism for a needle assembly, such as a Huber needle. A main body has a channel having a proximal end to encompass tubing and a distal end for positioning proximate a needle. The main body further has a first hinge mechanism and a first latching mechanism. A movable cover has needle receptacle, a second hinge mechanism connected with the first hinge mechanism of the main body, and a biasing member for pivoting movable cover about the first and second hinge mechanisms relative to the main body. The movable cover has a second latching mechanism to latch with the first latching mechanism in a closed position, in which the safety mechanism can be undocked from the needle and slid away from the needle along the tubing. The movable cover has a release mechanism to allow pivoting of the movable cover about the hinge mechanisms such that the needle receptacle of the movable cover at least partially receives the needle of the needle assembly in an open, locked position.

19 Claims, 21 Drawing Sheets

(56) References Cited

U.S. PATENT DOCUMENTS

| | | | |
|---|---|---|---|
| 6,921,388 B2* | 7/2005 | Swenson | A61M 5/3216 604/110 |
| 7,008,270 B1* | 3/2006 | Huh | G02B 6/3821 439/700 |
| 2001/0039401 A1* | 11/2001 | Ferguson | A61M 5/158 604/198 |
| 2003/0181874 A1 | 9/2003 | Bressler et al. | |
| 2004/0260250 A1 | 12/2004 | Harris et al. | |
| 2005/0049553 A1* | 3/2005 | Triplett | A61M 5/158 604/110 |
| 2005/0080386 A1 | 4/2005 | Reid | |
| 2005/0119635 A1 | 6/2005 | Crawford | |
| 2007/0066937 A1* | 3/2007 | Jones | A61M 5/158 604/110 |
| 2007/0088272 A1* | 4/2007 | Jones | A61M 25/0631 604/163 |
| 2008/0222896 A1* | 9/2008 | Marfione | B26B 1/048 30/157 |
| 2009/0299302 A1* | 12/2009 | Lambert | A61M 5/158 604/263 |
| 2010/0234804 A1* | 9/2010 | Hiejima | A61M 5/158 604/110 |
| 2011/0288482 A1* | 11/2011 | Farrell | A61M 5/326 604/164.04 |
| 2011/0301552 A1* | 12/2011 | Nakanishi | A61M 5/158 604/263 |
| 2012/0123332 A1* | 5/2012 | Erskine | A61M 5/158 604/110 |
| 2013/0046249 A1 | 2/2013 | Cowe | |
| 2013/0090626 A1* | 4/2013 | Feldtman | A61M 25/0074 604/510 |
| 2013/0172826 A1* | 7/2013 | Morita | A61M 5/00 604/263 |
| 2013/0237928 A1* | 9/2013 | Fisher | A61M 5/158 604/263 |
| 2013/0296804 A1* | 11/2013 | Lambert | A61M 5/158 604/263 |
| 2014/0135652 A1* | 5/2014 | Wilkinson | A61M 5/3269 600/576 |
| 2014/0135713 A1* | 5/2014 | Domonkos | A61M 5/3216 604/263 |
| 2014/0375946 A1* | 12/2014 | Rochford | G02C 5/006 351/63 |
| 2015/0105727 A1 | 4/2015 | Schweikert et al. | |
| 2015/0151054 A1* | 6/2015 | Wilkinson | A61M 25/0612 604/263 |
| 2015/0202412 A1* | 7/2015 | Nakajima | A61M 25/0631 604/263 |
| 2015/0231331 A1* | 8/2015 | Stroup | A61M 5/158 604/126 |
| 2015/0257693 A1* | 9/2015 | Baid | A61M 5/3271 604/263 |
| 2015/0297867 A1* | 10/2015 | Howell | A61M 25/02 604/174 |
| 2015/0314067 A1* | 11/2015 | Knobloch | A61M 5/3275 604/263 |
| 2015/0342639 A1* | 12/2015 | Wang | A61M 5/158 604/263 |
| 2016/0151088 A1* | 6/2016 | Hsu | A61M 5/158 604/263 |
| 2016/0317755 A1* | 11/2016 | Wang | A61M 5/3216 |
| 2017/0165421 A1 | 6/2017 | Lambert | |

* cited by examiner

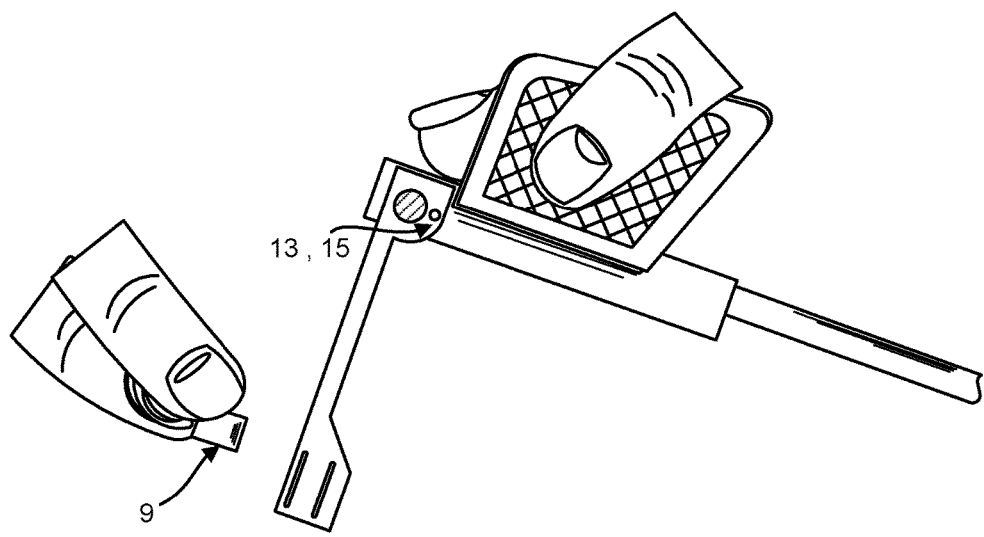
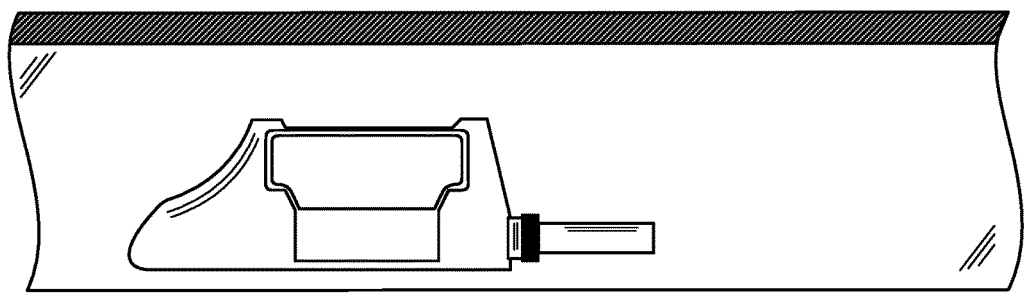
FIG. 17

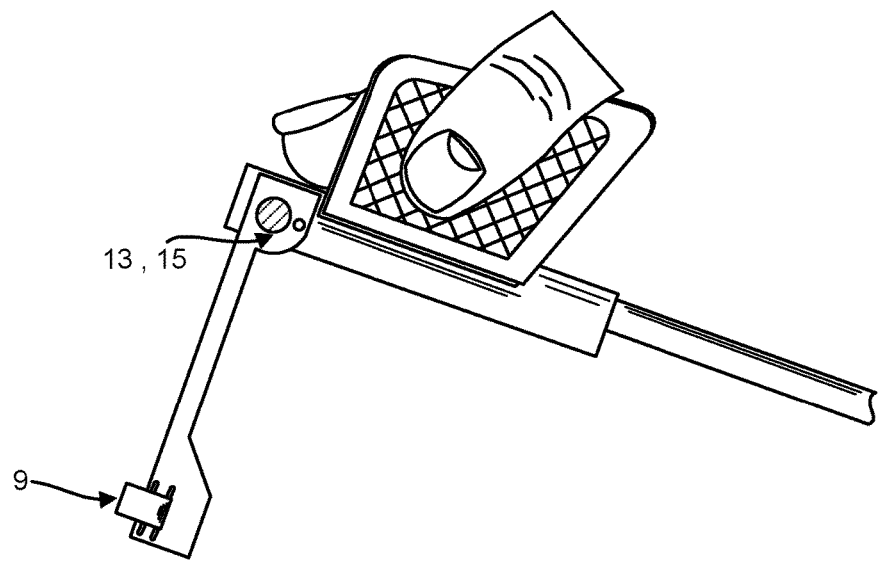
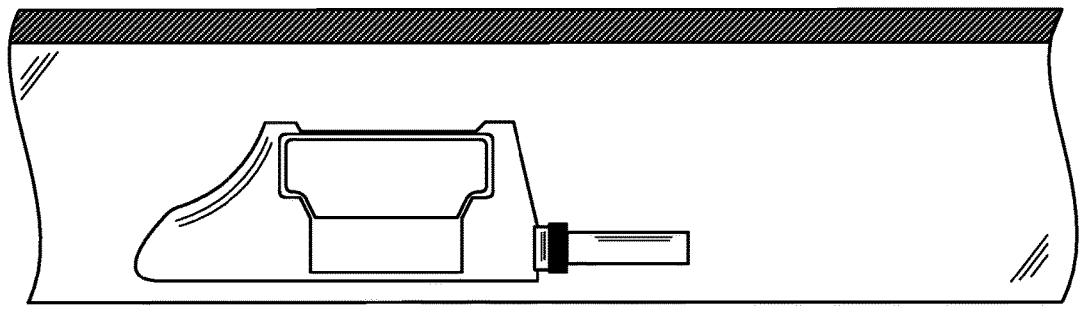
FIG. 19

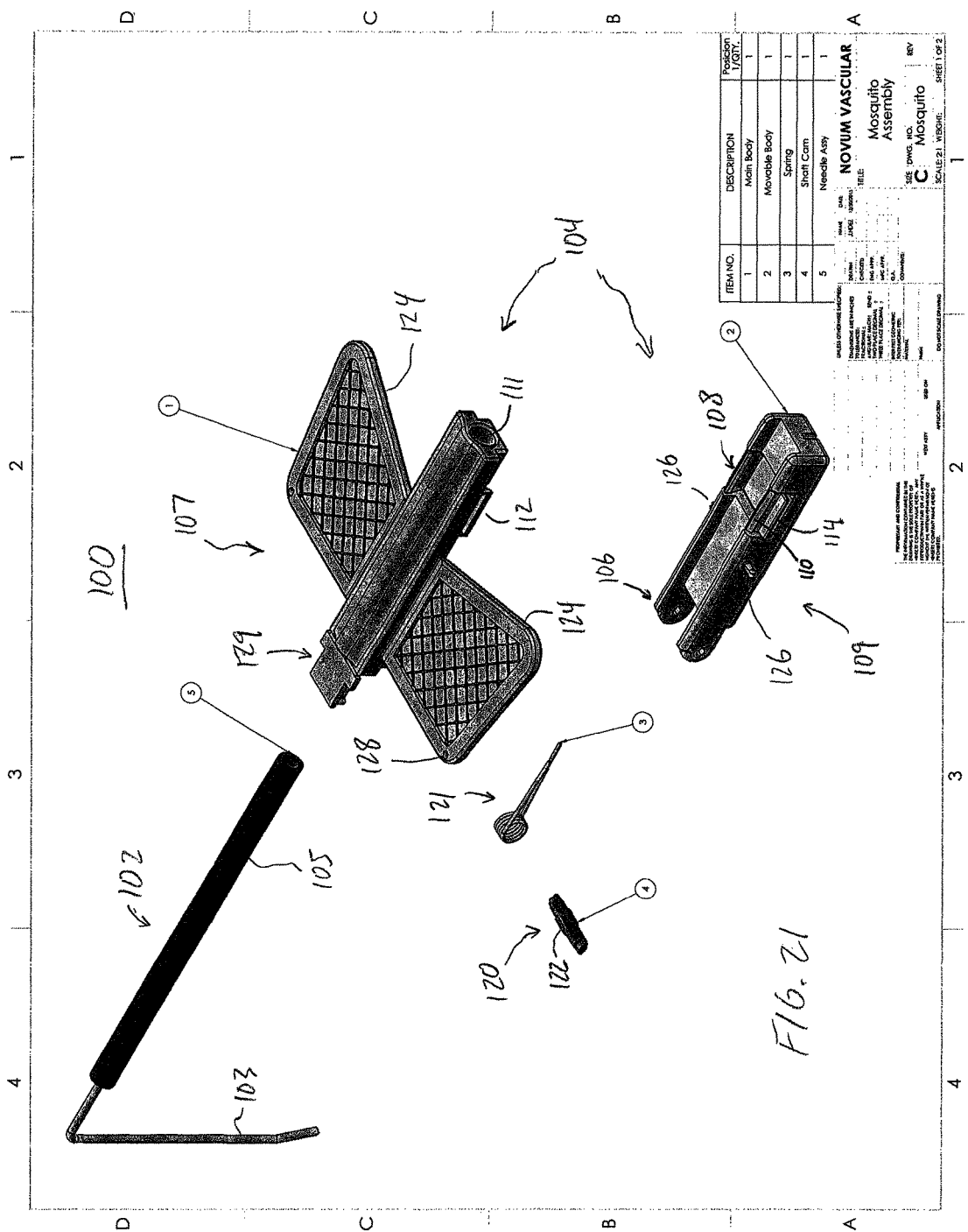

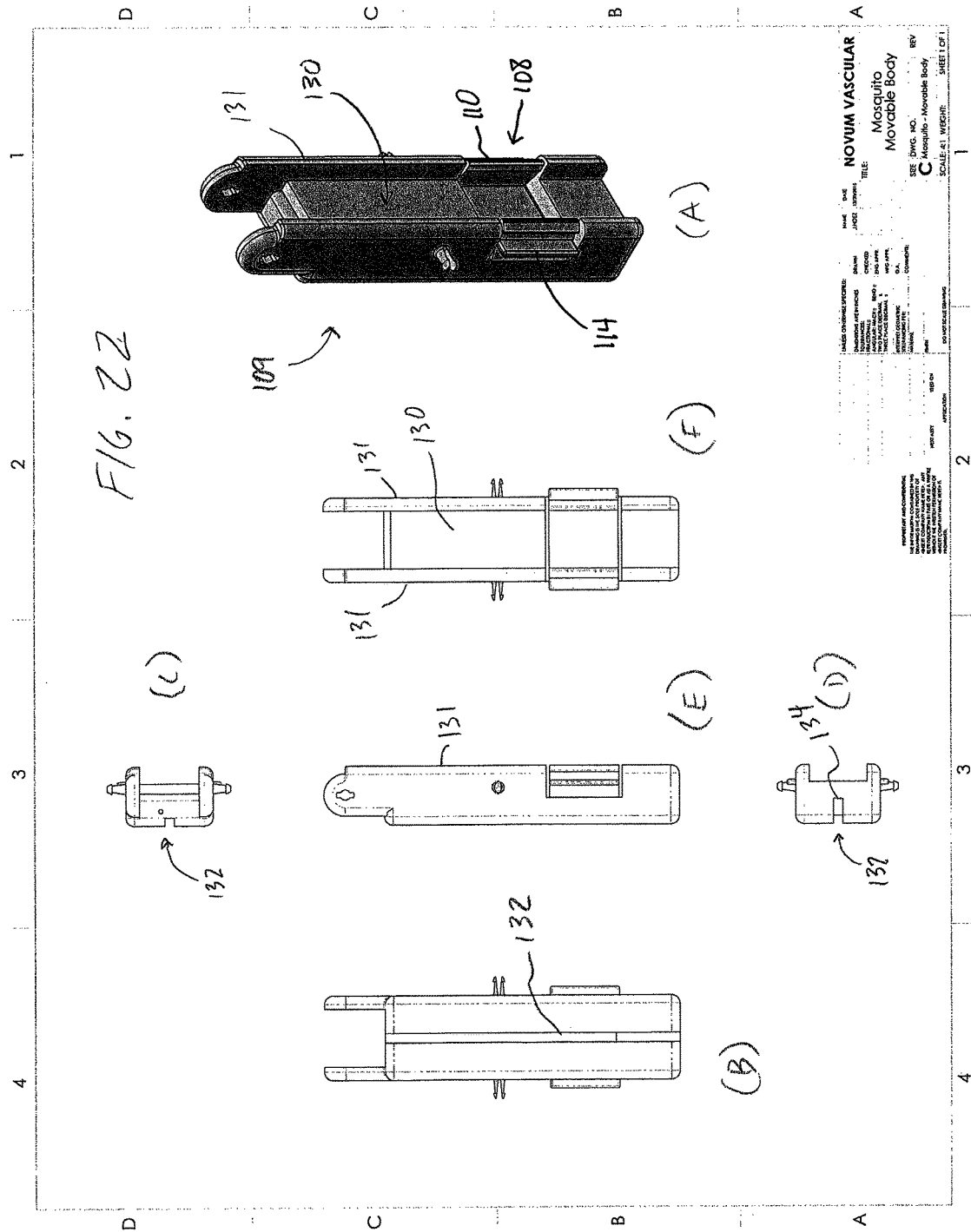

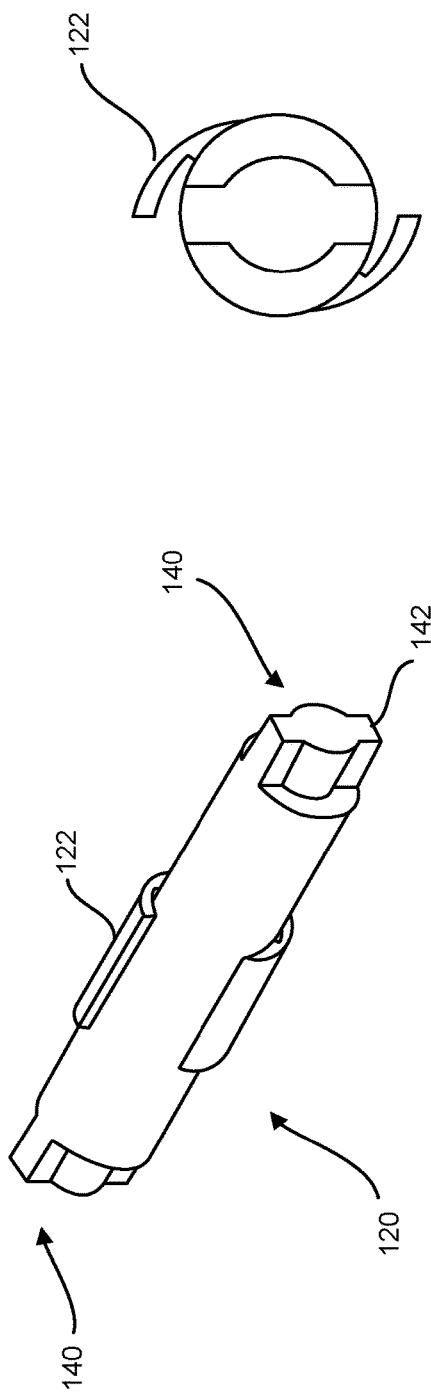
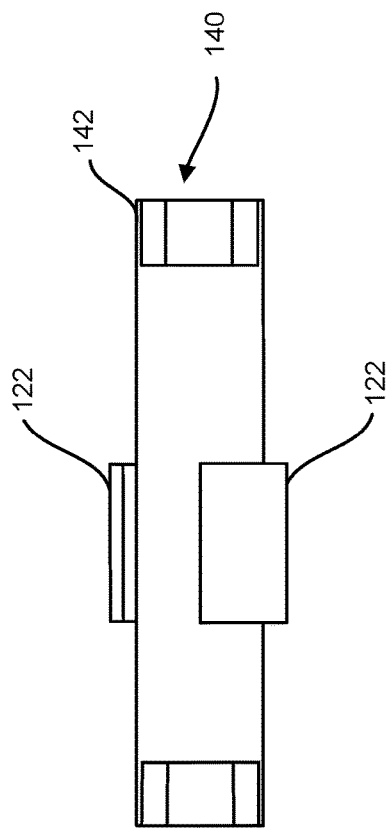
FIG. 24A
FIG. 24B
FIG. 24C

PASSIVE SAFETY HUBER NEEDLE

BACKGROUND

The present invention relates to Huber needle assemblies, and more particularly to a safety device for a Huber needle assembly.

With the passage of the needlestick safety act (Public Law 106-430, 106th Congress, H.R. 5178) with an effective date of Apr. 18, 2001, the Occupational Safety and Health Administration (OSHA) now requires affected employers, primarily healthcare institutions, to consider and implement new technologies when they update their "exposure control plan." Included are "engineering controls" (devices) to mitigate the possible exposure to blood-borne pathogens via accidental needle sticks.

Various engineering controls exist to protect nurses, technicians and caregivers from accidental needle sticks from injection needles, venous cannulation devices, skin closure devices and scalpels. In the area of subcutaneous medication device access (port), in which a Huber needle assembly is employed, a number of devices exist that offer a margin of protection from accidental needle sticks when removing the needle, or "sharp," from the port. One danger from de-accessing a subcutaneous port is the result of how the port itself is constructed. The port is a metal or plastic device with a pierceable area, often made of a silicone compound, through which access is made by a Huber needle to the vascular system for the purpose of infusing medication into the body. The Huber needle is specially designed to reduce the possibility of mechanically damaging and/or removing a portion of the the pierceable area as it is punctured, and which is referred to as "coring." This coring limits the number of times a port can be accessed. To combat this damage and extend the useful life of the port, the silicone compound is inserted under pressure into the device. It is this pressure that is the arbiter of the danger to the clinician removing the needle used to cannulate the port.

There are some devices that provide at best limited protection to a clinician when removing the needle. For instance, in some devices, a safety capture device uses a latching feature such as "hooks" or "fingers" that are manually secured around the needle by forcing the needle between them. But these devices require the clinician to grasp the needle with one hand, and secure it with a latching cover with the other hand. These devices can be rearmed by simply defeating the latching feature, such as spreading the hooks or fingers, which could release the needle.

Another danger in removing the needle is the resistance to extraction exerted on the needle by the compressed silicone compound on the port the needle inhabits. Due to this resistance, the clinician may use both hands to remove the needle to prevent pain at the insertion site as well as manipulate the safety capture device to safely cover the needle. When the needle "clears" the resistance of the silicone barrier the individual removing the needle will involuntarily compensate for the loss of resistance by reversing the motion and redirect the needle back towards the patient and their fingers being used to stabilize the area of the patient's skin surrounding the subcutaneous port.

The other problem with these designs is that the force necessary to push the needle through the latching cover is substantial. If the clinician uses a strong enough spring to force the needle through the capture feature to assure a 100% capture rate it could pinch the patient as the swing arm travels and "pins" some sensitive skin between the partially indwelling needle and the arm of the safety device. If you use a weaker spring you run the risk of not having the needle force necessary to spread the fingers and secure the needle. Not unlike a yard gate latch that incorporates two opposing "hooks" held in closure by a spring. The latch pin attached to the gate section has to overcome the force of the spring to spread the hooks to engage the latch.

No passive device existed that would allow a single clinician remove and flush the device at the same time.

SUMMARY

As previously stated, there are a number of devices that provide a method to cover the needle after extraction. However, all require the clinician to use both hands to complete the removal and protection sequence, requiring an additional clinician if there is a need or desire to flush the needle during extraction. Therefor until the complete removal and subsequent protection maneuver is completed, the clinician remains at risk.

This device differs in that it is rendered safe at the point of removal. It is the design and function of passively rendering the needle safe and locking the safety device at the instant it exits the skin that primarily sets this device apart from other similar or related designs. A distinctive feature of this device is the ability for a sole clinician to initiate removal of the device and complete the removal, flushing and sharp protection process without assistance.

This "passive" sharp coverage and integral locking system represents an important advance in the safety of using such devices. As previously mentioned, with this device, one hand of the clinician can be freed to deliver a small amount of flush solution to prevent retrograde blood flow into the catheter connected to the port. The negative pressure is created by the decrease in volume of fluid in the port so created by the removal of the needle from the confined space of the port. This flushing technique is recognized as an important step in the prevention of thrombus formation and occlusion of the fluid conduit or catheter extending from the port to the central vascular termination point.

The height profile of this device is also a feature which is unique to safety versions of Huber point needles with attached extension sets and stabilization wings. The overall height profile of this invention is roughly the same as non safety devices with attached extension sets and stabilization wings configured in the same manner.

In one aspect, a safety mechanism is presented and described for a Huber needle assembly having tubing and a needle extending from a distal end of the tubing. The safety mechanism includes a main body having a distal end, a proximal end, opposing side walls, and a securement door coupled at the distal end of the main body to dock the main body to the needle when the securement door is closed. The main body defines a channel to at least partially encompass the tubing and enabling the main body to be de-docked from the needle and slid along the tubing for being positioned between the needle of the Huber needle assembly and an inlet of the tubing when the securement door is open. The main body further has a first hinge mechanism near the distal end of the main body and a first latching mechanism toward the proximal end of the main body.

The safety mechanism further includes a movable cover having a needle receptacle, a second hinge mechanism connected with the first hinge mechanism of the main body by a cam lock axle, and a biasing member for pivoting the movable cover about the first and second hinge mechanisms relative to the main body. The movable cover further has a second latching mechanism to latch with the first latching mechanism in a closed position to retract the movable cover to engage with a bottom side of the main body. The movable cover further has a release mechanism to release the latching between the first and second latching mechanisms to allow the pivoting of the movable cover about the first and second hinge mechanisms such that the needle receptacle of the movable cover at least partially receives the needle of the needle assembly in an open position The details of one or more embodiments are set forth in the accompanying drawings and the description below. Other features and advantages will be apparent from the description and drawings, and from the claims

BRIEF DESCRIPTION OF THE DRAWINGS

These and other aspects will now be described in detail with reference to the following drawings.

FIG. 17 illustrates the needle assembly completely removed from the port and patient tissue with the needle now covered by the safety mechanism automatically locked to prevent any accidental reuse or re-exposure to the needle.

FIG. 19 illustrates the needle assembly completely removed from the port and patient tissue with the needle now covered by the safety mechanism automatically locked to prevent any accidental re use or re exposure to the needle now with the safety mechanism arming device reattached as a final locking device.

FIG. 21 illustrates a safety needle system that includes a safety mechanism for a needle assembly, such as a Huber needle.

FIGS. 22A-22F show various views of a movable cover of the safety mechanism.

FIGS. 24A-24C show various views of a cam lock axle and shaft, that locks the movable cover in an open position from the main body, for passive safety from the needle.

Like reference symbols in the various drawings indicate like elements.

DETAILED DESCRIPTION

This document describes a passive cannula protection device for subcutaneous infusions and implanted vascular access devices.

Figure 1:
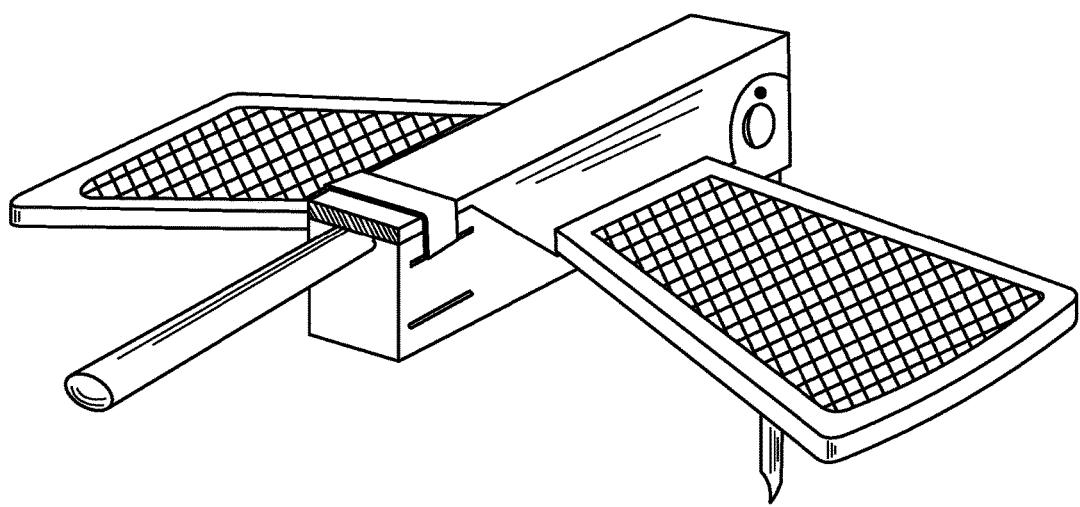
FIG. 1 illustrates an oblique view of a needle assembly and safety mechanism in accordance with some implementations.
Figure 2:
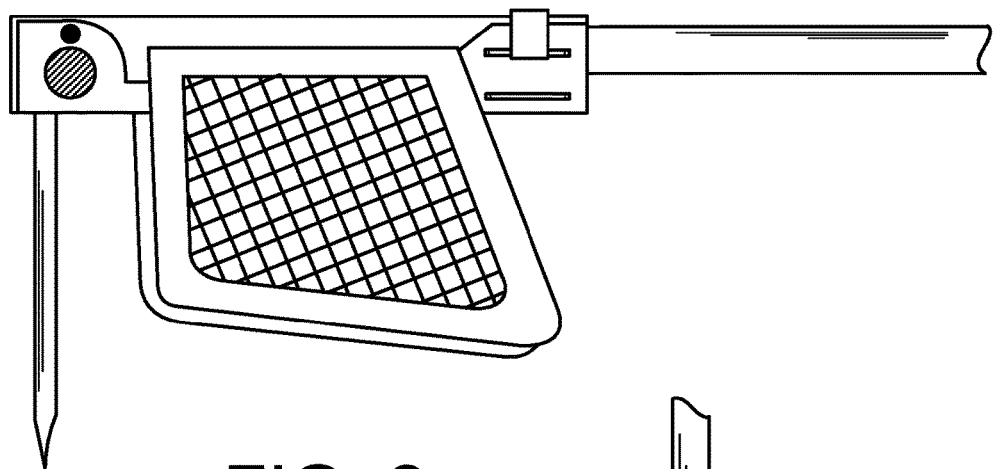
FIG. 2 illustrates a side view of the needle assembly and safety mechanism in accordance with some implementations.
Figure 3:
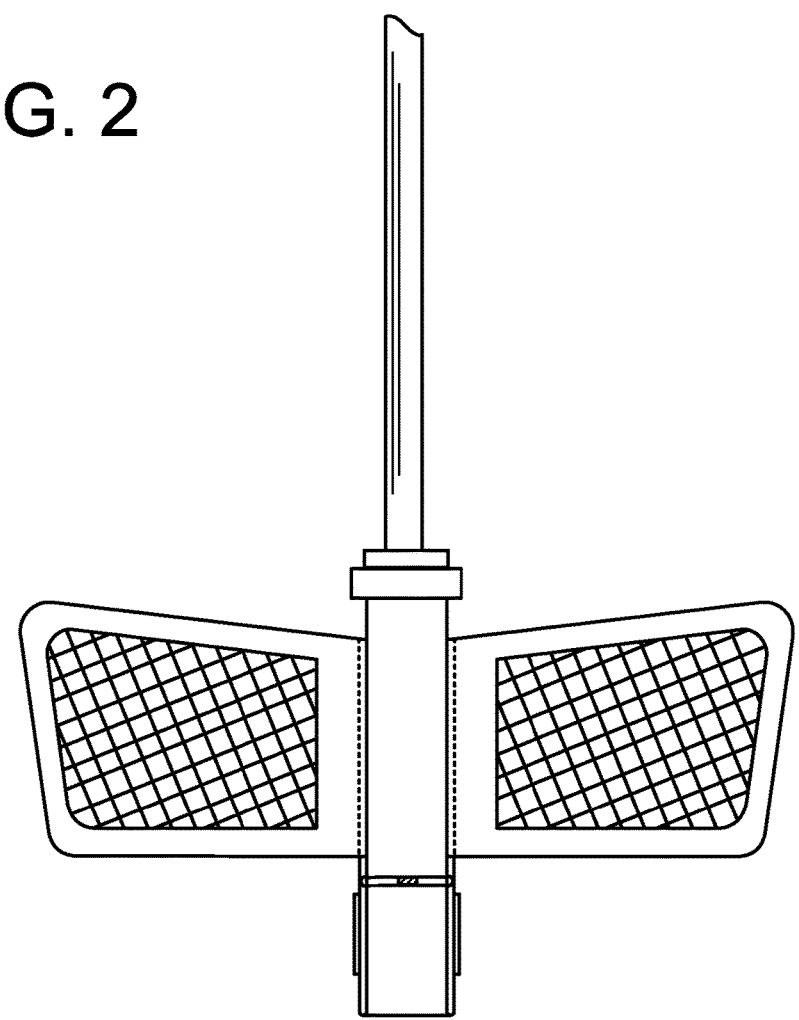
FIG. 3 illustrates a top view of the needle assembly and safety mechanism in accordance with some implementations.
Figure 4A:
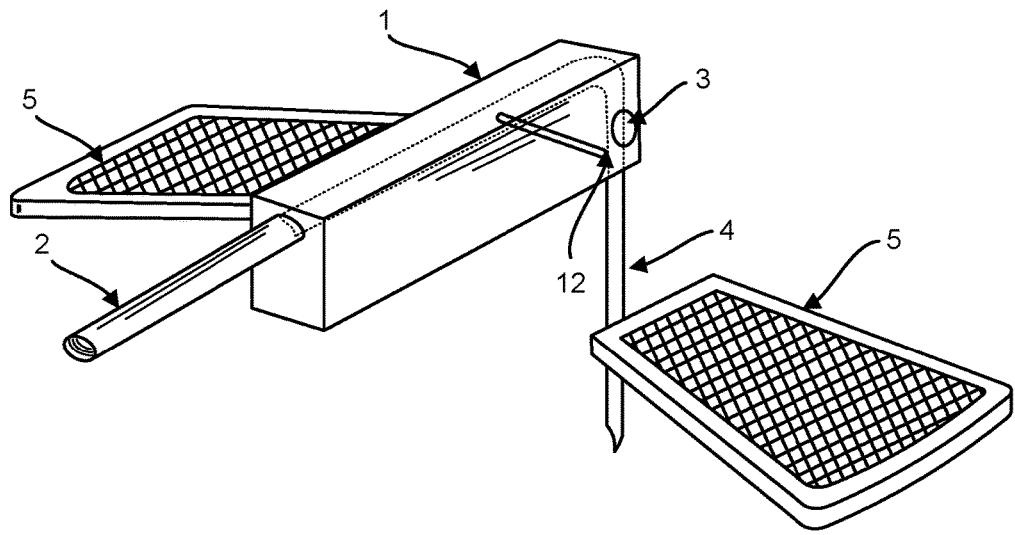
FIGS. 4A-4B illustrates a side oblique view of a needle assembly and safety mechanism in accordance with some implementations, with one of the wings and the body of the safety mechanism detached to illustrate features.
Figure 4B:
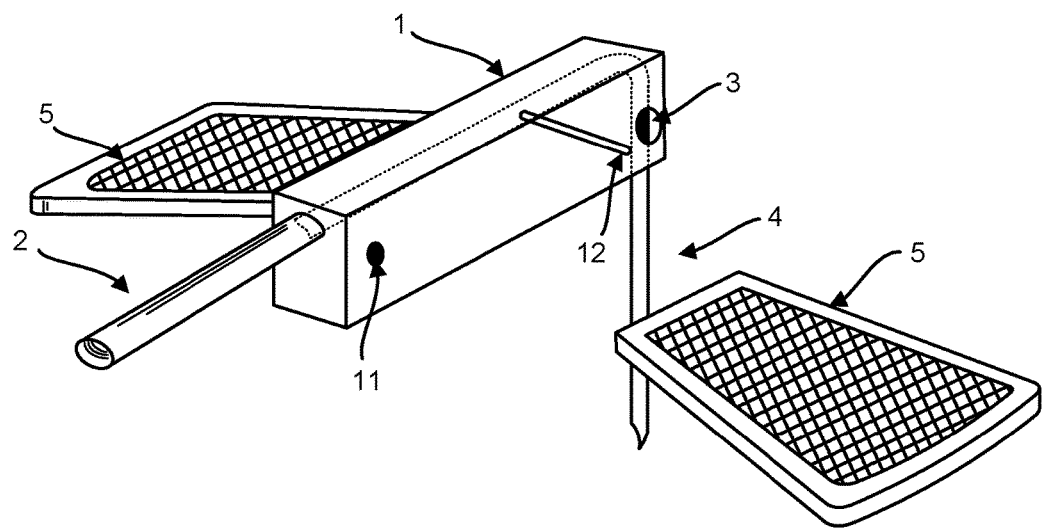

The device shown in FIGS. 1, 2, and 3 is an assembled needle assembly and safety mechanism. FIGS. 4A-4B show a needle assembly and safety mechanism having a main body 1 which contains the 4. Huber needle 5, one or more stabilization wings 3, and a conduit through which an axle 12 is positioned for attaching the safety mechanism and a propulsion bar to the main body 1. Also shown is a channel through which the safety mechanism excursion locking clip 9 spans the distal plane of the assembly connecting the main body 1 to the safety mechanism.

Figure 5A:
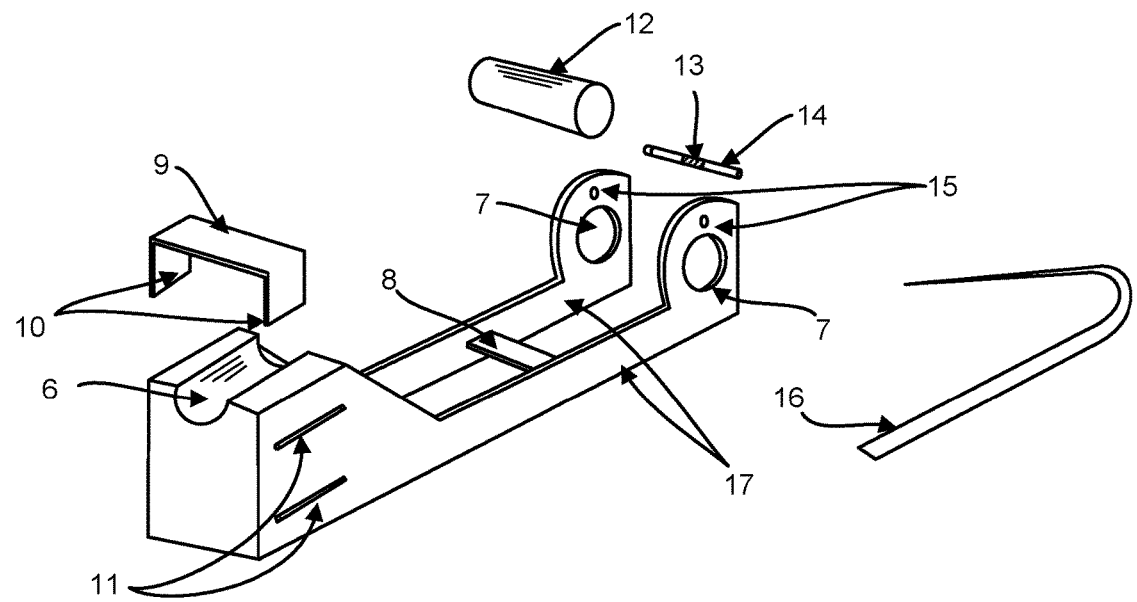
FIGS. 5A-5B illustrates some implementations of a safety mechanism for a needle assembly with depictions of integral parts detached or disassembled.
Figure 5B:
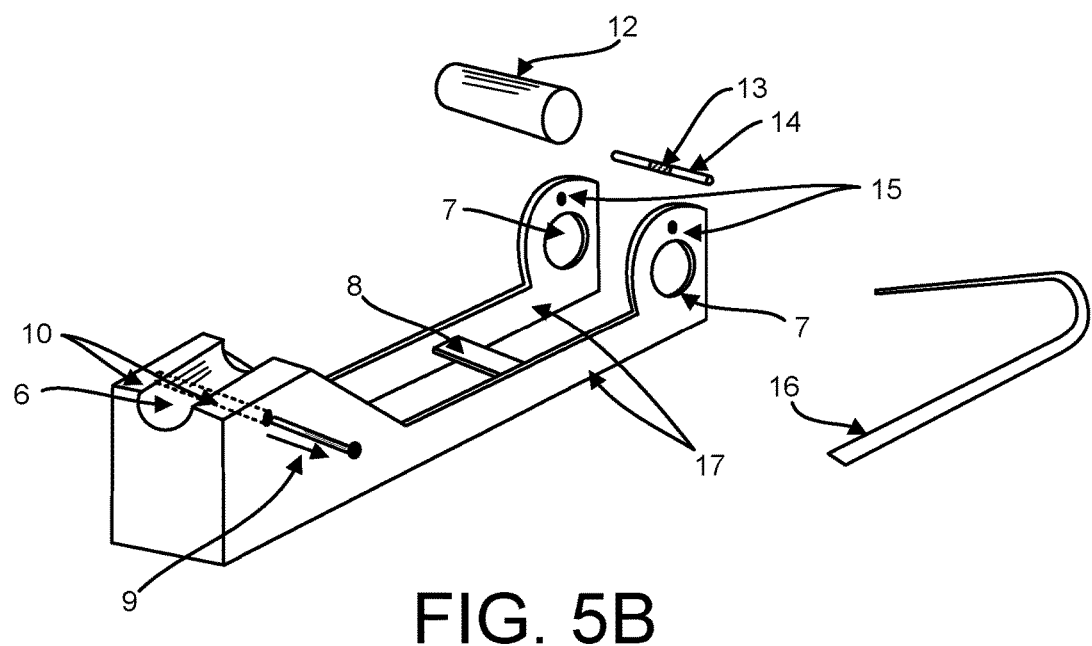
Figure 6:
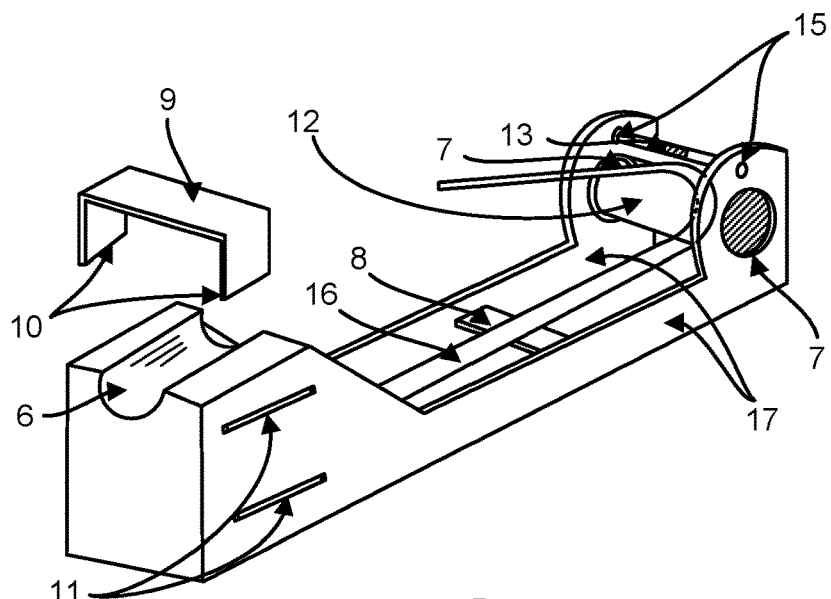
FIG. 6 illustrates FIGS. 5A-5B with the integral parts assembled.

FIGS. 5A-5B illustrate the safety mechanism. The safety mechanism is connected to the main body 1 via the axle 12 which spans the main body 1 via the conduit 3 and attaches to the safety mechanism by way of penetrating aperture 7. This implementation relies on a friction fit to maintain fixation of the main body 1 to the safety mechanism. The propulsion bar 16 exerts pressure on the arms of the security feature via 8 the stabilization strut and the bottom of main body 1 to urge the safety mechanism to passively enclose the needle 4. An activation/securement clip 9 spans the main body 1 to secure the safety mechanism to the main body 1 until such time that the entire device is to be removed from the port, as shown in FIG. 6. The safety mechanism is primarily disabled by a locking shaft 14 urged into the locking position by an integral compressed expansion mechanism which expands the length of locking shaft 14 to urge it to penetrate openings 5 on the safety mechanism, as the safety mechanism reaches full excursion having been urged there via the propulsion bar 16.

Figure 7:
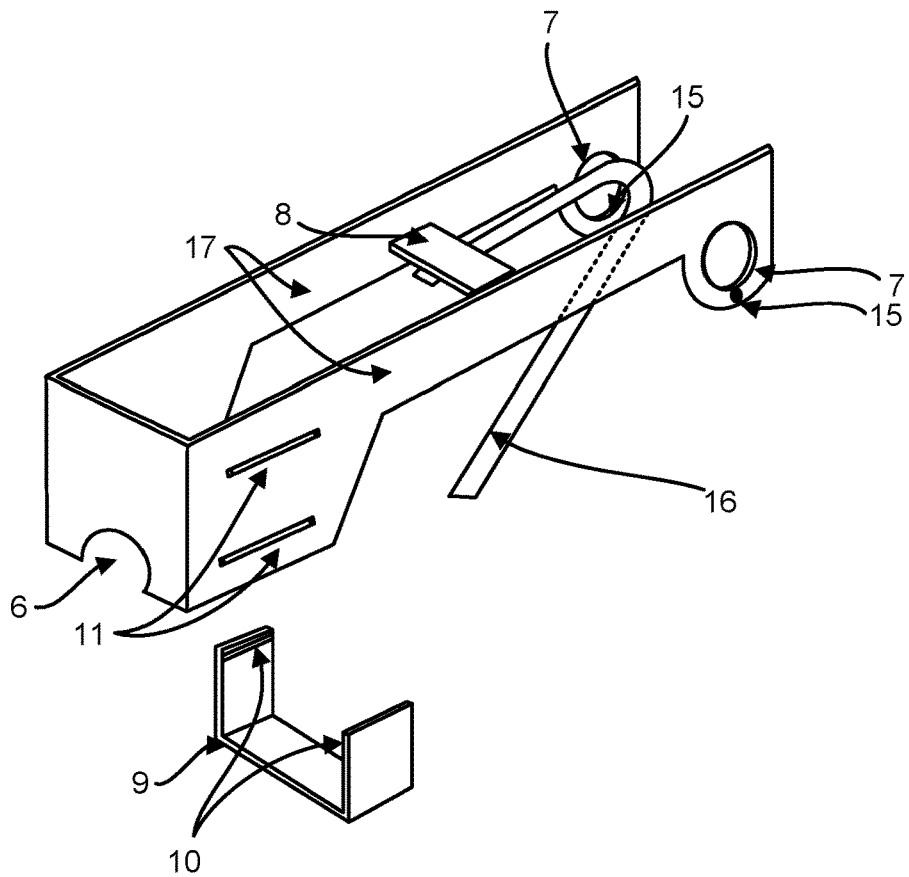
FIG. 7 illustrates an upside down view of FIG. 6

FIG. 6 is a detailed view of the safety mechanism having two arms each terminating on one end with an aperture 7 through which the axle 12 allows the safety mechanism mobility. An expandable retaining bar 14 retains the propulsion bar 16, or other biasing member such as a spring, and also connects the safety mechanism to the main body 1. Located above the apertures 7 are locators 15 which accept the end of 11 as it expands to occupy axle 12 as the safety mechanism reaches maximum excursion during the removal process and apertures 11 align. The propulsion bar 16 moves the entire safety mechanism from its resting position by exerting force against the bottom of the main body 1 and the safety mechanism arm stabilization bar 8. The tubing channel 6 accommodates the medication supply tubing 2 in an unrestricted fashion as it exits the main body 1. The safety mechanism activation clip 9 maintains the safety mechanism in an unreleased position until removed. The safety mechanism activation clip 9 is aided in retention of the safety mechanism by flanges 10 that can engage channels 11 molded or formed into the outer surface of the proximal end of the safety mechanism. The safety mechanism activation clip 9, if reserved, may be reattached to the safety mechanism, after having been rotated 90 degrees on its longest axis, to add addition security to needle retention accomplished by locking at the point of maximum excursion of the safety mechanism. FIG. 7 is a view of the safety mechanism, described in greater detail above and with reference to FIG. 6, having been rotated approximately 180 degrees on its longest axis.

Figure 8:
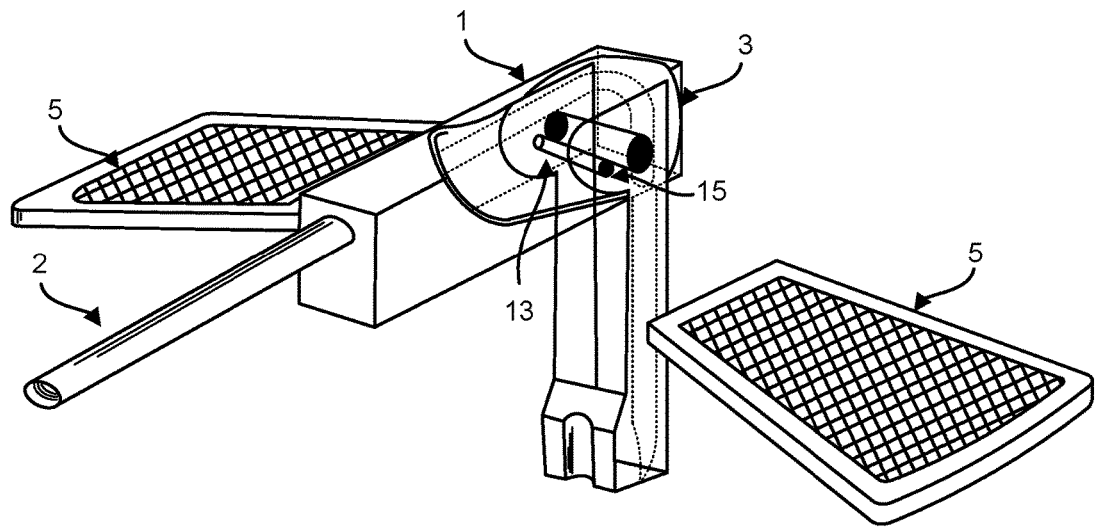
FIG. 8 illustrates a cutaway view of the integration of the safety mechanism and locking mechanism that disables the device when the safety mechanism is in the final position.

FIG. 8 is an internal view of the integration of a locking mechanism having a cam shaft 13 that extends through receptacles 15, and which locks the needle shielding safety mechanism from being able to be retracted and result in the possible exposure of the care giver to the sharp or the intentional reuse of the device. The locking pin 14 is urged into an extended position engaging it with the apertures 15 to complete the initial locking sequence.

Figure 9:
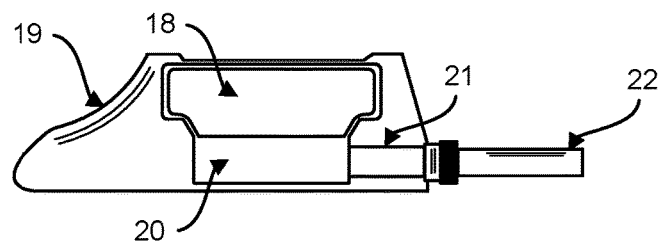
FIG. 9 illustrates an example of an implantable subcutaneous vascular access device, commonly and herein referred to as a port.

FIG. 9 is a simple cross sectional view of an example of a subcutaneous vascular access device or port 5. The subcutaneous vascular access port 5 includes a pierceable area 18, such as a membrane of a silicone compound or the like, a housing that includes a top opening that is occupied by the pierceable area 20, a reservoir that receives a fluid via the pierceable area, and a conduit 21 to intravascular tubing 22.

Figure 10:
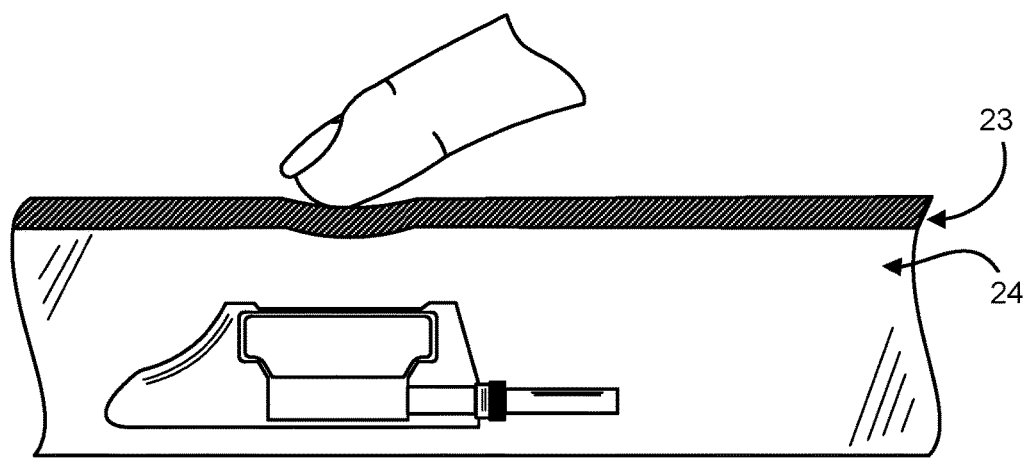
FIG. 10 illustrates an example of the port within the subcutaneous tissue and a rough example of how to locate the margins of the device using palpation of the skin with the index finger.
Figure 11:
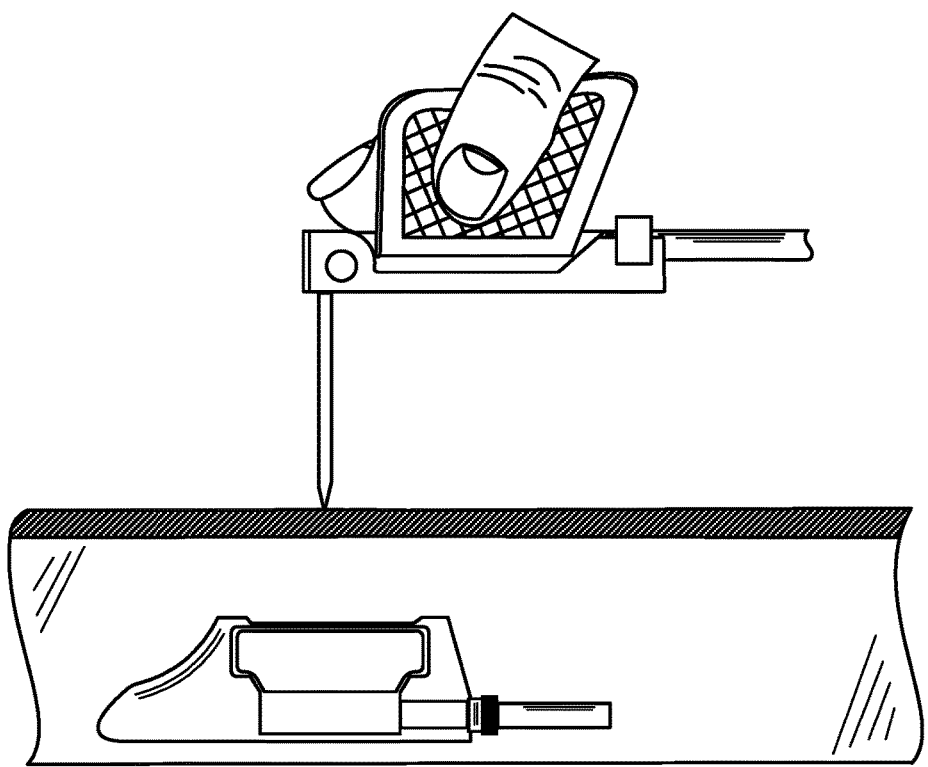
FIG. 11 illustrates an example of a preferred method of grasping the needle assembly with safety mechanism, and positioning the needle assembly for insertion into the port.

FIGS. 10-19 illustrate a method of using a passive safety Huber needle system in accordance with implementations described herein. FIG. 10 is a cross sectional view of subcutaneous vascular access port 5 in place in the subcutaneous tissue, and illustrating a method of locating the port below the skin 23 and within the subcutaneous tissue 24 using pressure exerted on the skin 23 and subcutaneous tissue 24 with a finger, in accordance with one preferred exemplary implementation. FIG. 11 illustrates one preferred method of grasping the invention and positioning it for insertion into the port.

Figure 12:
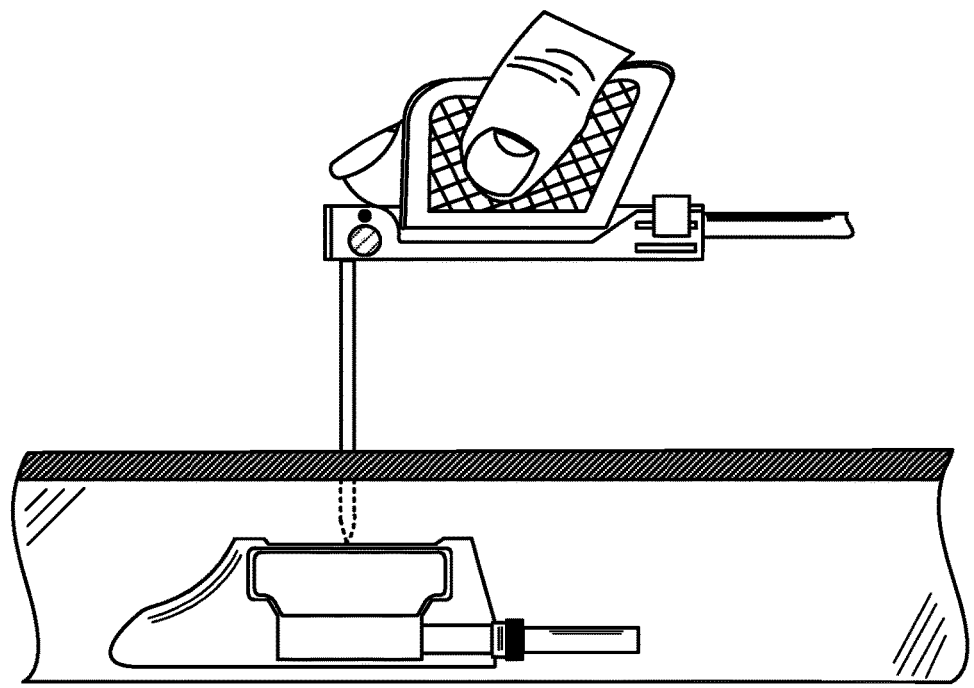
FIG. 12 illustrates the progress of the needle through the skin and subcutaneous tissue to a location immediately prior to entering the silicone entry dome of the port.
Figure 13:
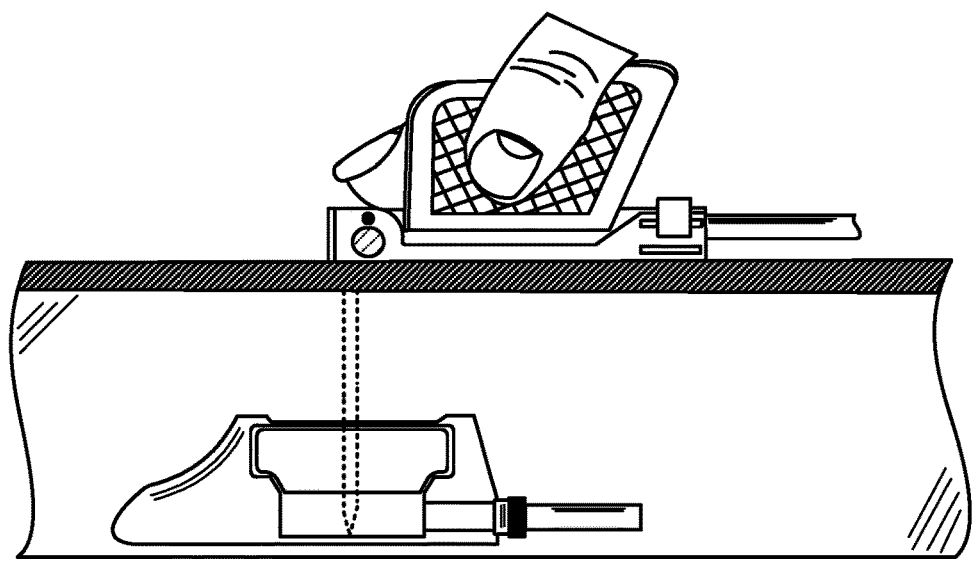
FIG. 13 illustrates the best final position in the port.
Figure 14:
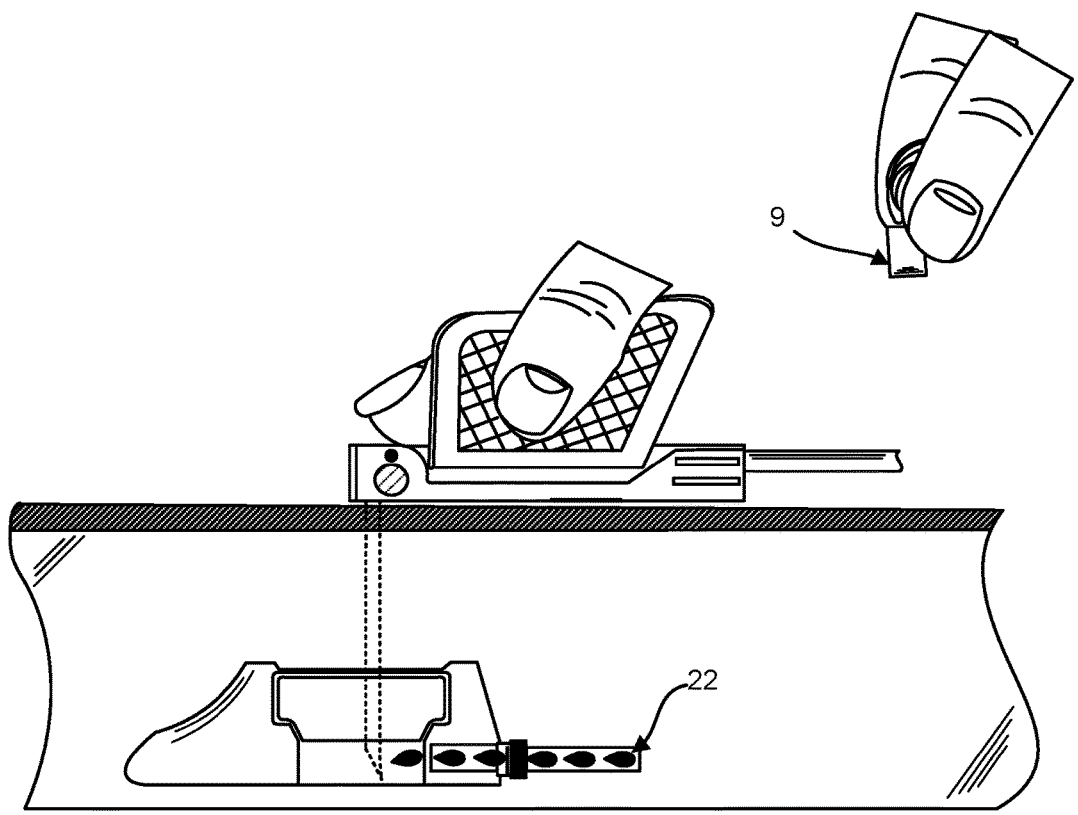
FIG. 14 illustrates the activation of the safety mechanism of this embodiment of the invention immediately prior to removal from the port by removing the clip confining the main body and the safety mechanism.

FIG. 12 illustrates a step of insertion of the Huber needle into the port. FIG. 13 illustrates a further progress of inserting the Huber needle into the port, and demonstrating an ideal final position. FIG. 14 illustrates the initiation of the sequence of removal of the needle from the port and a subsequent protection of the Huber needle by the safety mechanism. The sequence is initiated by the removal of the safety mechanism activation clip 9 and to begin the flushing via the intravascular tubing 22 of the system with a clinician's free hand. The safety mechanism activation clip 9 can be reserved for later use.

Figure 15:
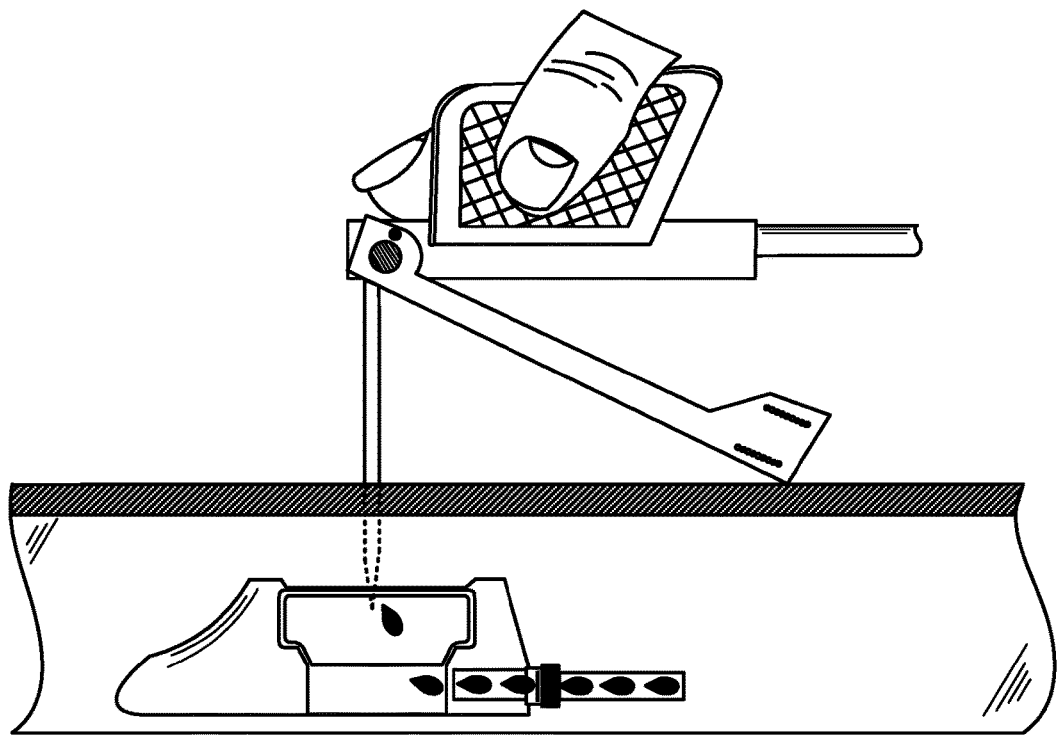
FIG. 15 illustrates again the preferred method of grasping the invention during the extraction process with the safety mechanism excursion in progress.
Figure 16:
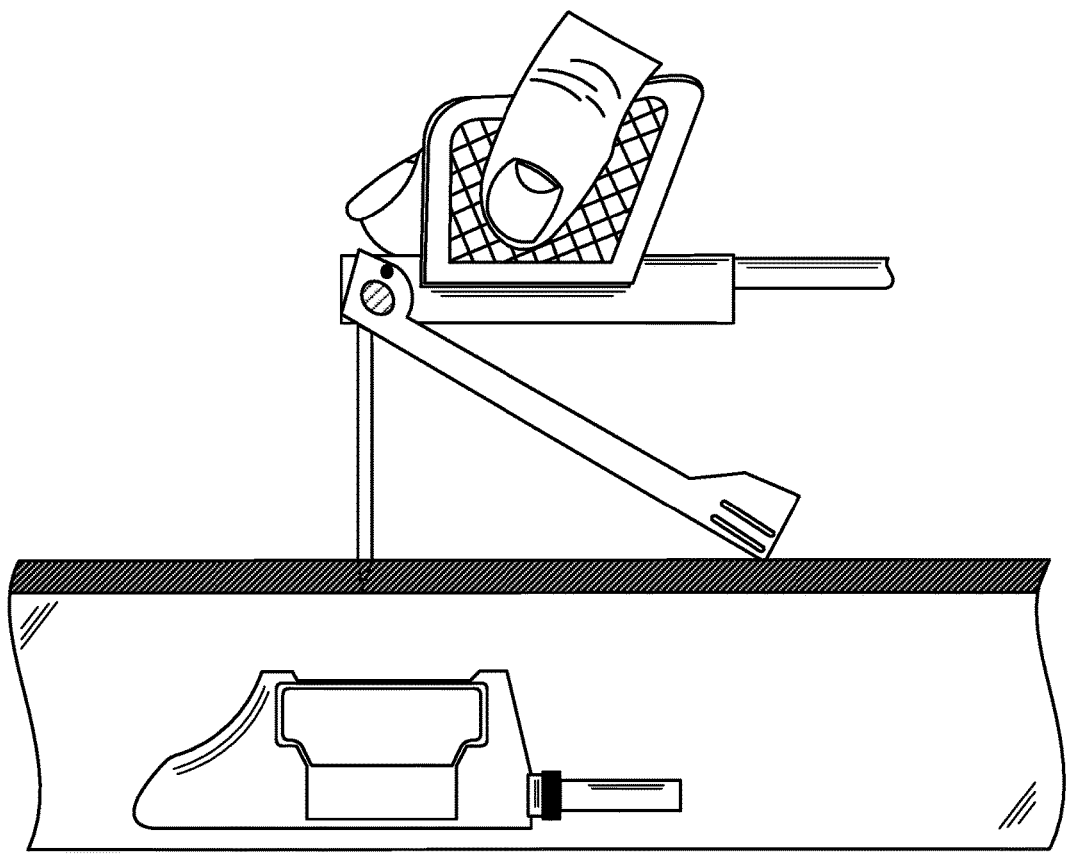
FIG. 16 illustrates the needle assembly being further extracted from the port and the continued progress of the safety mechanism en route to the final lock position covering the needle.

FIG. 15 illustrates a grasp and removal of the needle from the port. Demonstrated also is the passive activation of the safety mechanism en route to cover, and with the locking mechanism, permanently shield the needle by the safety mechanism. The passive movement of the safety mechanism, without active intervention by the clinician, allows the clinician to utilize the free hand to inject fluid into the tubing 2 to replace the physical volume within the port displaced by the needle 4. FIG. 16 further illustrates the removal of the needle from the port and passive movement (i.e. without active clinician intervention) of the safety mechanism en route to cover and protect the needle.

Figure 18:
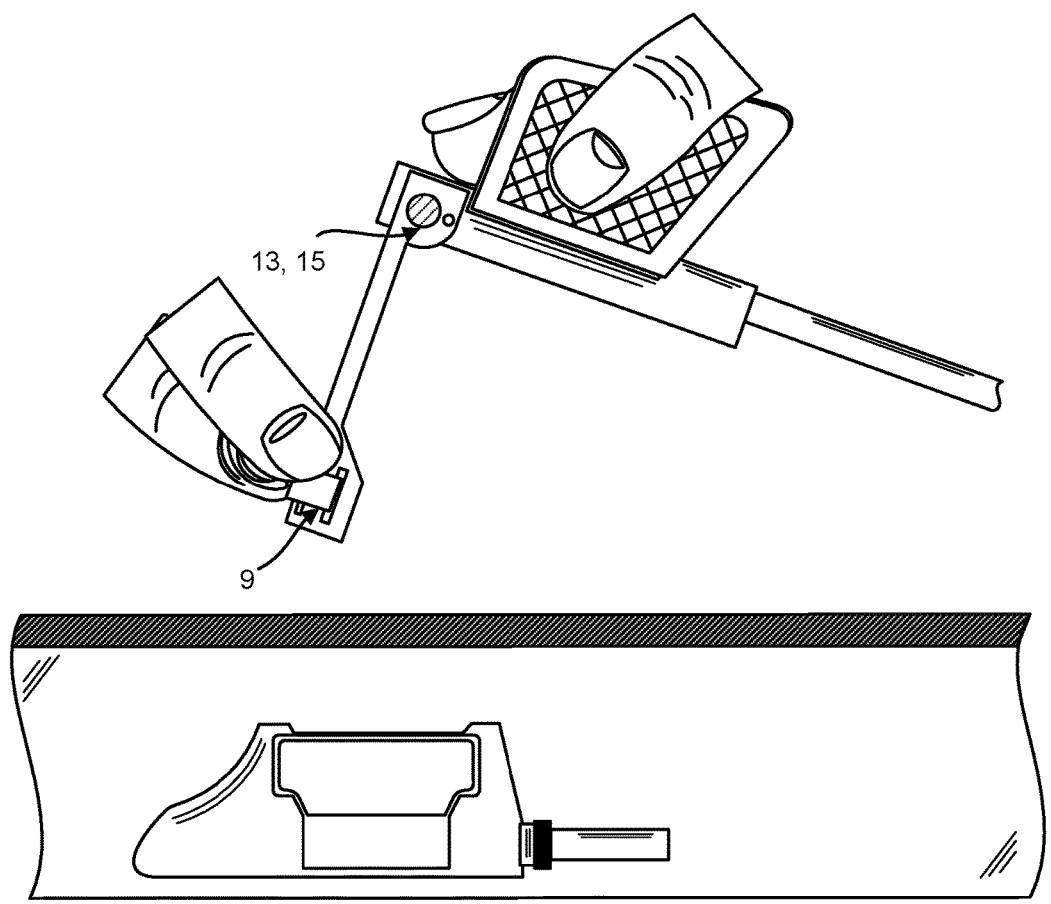
FIG. 18 illustrates the needle assembly completely removed from the port and patient tissue with the needle now covered by the safety mechanism automatically locked to prevent any accidental reuse or re-exposure to the needle now with the safety mechanism arming device being reattached as a final locking device.
Figure 20:
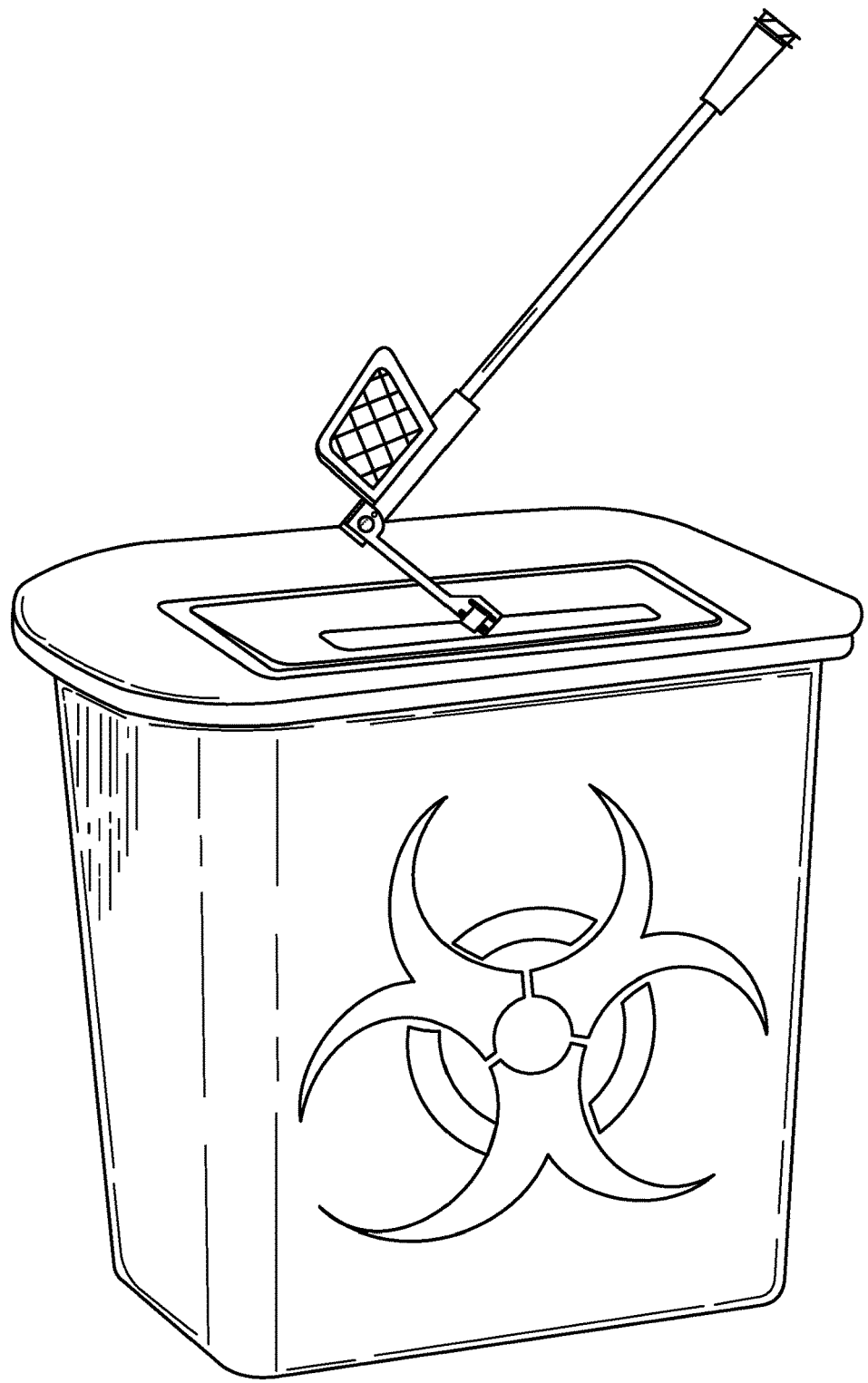
FIG. 20 depicts disposal of the device in a sharps container with the safety mechanism activated.

FIG. 17 illustrates the completed removal of the needle from the port and the completed travel of the safety mechanism to the final open position, with expanded into and locking the safety mechanism in place covering the needle 4 and protecting the clinician from accidental exposure to the sharp. In some implementations, the activation clip 9 can be reattached to the safety mechanism to maintain the safety mechanism in an opened, locked and safe position, as an additional margin of safety in covering and securing the needle. FIG. 18 illustrates the safety mechanism being locked into place. This locking can be an internal mechanism, or by safety clip 9 that is placed on the safety mechanism. FIG. 19 illustrates the Huber needle being covered by the safety mechanism, which is locked in place by a locking mechanism. FIG. 20 illustrates the disposal of the subject device in the preferred embodiment in an example of sharps disposal container. In alternative implementations, the stabilizations wings can be folded down and attached to the safety mechanism to actually form a sharp containment device, as further described below.

FIGS. 21-25 illustrate some particular implementations of a safety needle system 100, in accordance with the descriptions above. As shown in FIG. 21, the safety needle system 100 includes a safety mechanism 104 for a needle assembly 102. The needle assembly 102 can be, without limitation, a Huber needle assembly (shown), which includes a Huber needle that is specifically designed and formed to penetrate a patient's skin and a subcutaneous vascular access port with minimal coring damage, although other needles can be employed by the safety needle system 100. The needle assembly 102 can include a needle 103 that extends from tubing 102. In the case of a Huber needle, the needle 103 can include a substantially right angle bend away from an axis defined by an end of the tubing 102, and a sharp distal end that is formed (i.e. bent) and adapted to allow ease of penetration of skin and/or port while minimize coring of each.

The safety mechanism 104 of the safety needle system includes a main body 107 coupled with a movable cover 109. The main body 107 includes and/or defines a channel 111 through which the tubing 105 extends. In some implementations, the channel 111 is sized and adapted for a tight fit around the tubing 105, however in some preferred implementations the channel 111 provides at least some clearance around the tubing 105 such that the main body 107 can be moved or slid up and down a length of the tubing, toward and away from the needle 103, respectively. In some implementations, the channel 111 can be formed to have a tolerance around the tubing 105 that provides a predetermined coefficient of friction for relative ease or difficulty in sliding the main body 107 relative to the tubing 105. In some preferred exemplary implementations, the channel 111 only extends from a proximal end of the main body 107 to a point between the proximal end and distal end of the main body 107, the point corresponding to an end point of the tubing from which the needle extends.

The main body 107 includes one or more stabilization wings 124 that extend outward from the main body 107. In some implementations, the stabilization wings 124 can take the form of "butterfly wings" found on some conventional vascular access devices, but which also include additional functionality. The stabilization wings 124 can be pivoted up to be grasped by in the fingers of a clinician, or pivoted downward to be applied on the skin of the patient. As added functionality, the stabilization wings 124 can include a securement mechanism 128 that can be secured with a corresponding securement mechanism 126 on the movable cover 109.

In some implementations, the movable cover 109 is connected to the main body 107 at a hinge 106 and latched together with the main body 107 at latches 108. The movable cover 109 can be connected with the main body 107 at hinge 106 by a cam lock axle 120, and biased to an open position by biasing member 121, which can be a spring, lever, or other biasing member. The biasing member 121 can include a spring that is wound around the cam lock axle 120, and include two distal arms on either side of the spring, one of each being connected respectively to the main body 107 and the movable cover 109. Other biasing mechanisms can be employed, such as latches, biased curved members (made of plastic, metal, or other rigid or semi-rigid material).

Each of the latches 108 of the movable cover 109 includes at least one releasable latching mechanism 110, such as a pin, flange, tooth, protrusion or other latching mechanism, to releasably engage with a corresponding receptacle 112, such as a hole, aperture, groove, channel, or the like, on the main body 107. The latching mechanism 110 can be associated with a release mechanism 114, such as a button, pin, switch, spring-loaded cam, flange, or the like, which can be operated by a finger of a clinician to release the latching mechanism 110 from the corresponding receptacle 112 and allow the movable cover 109 to pivot about the hinge 106 under force of the biasing member 121. In alternative implementations, the latching mechanism 110 described above can be formed on or associated with the main body 107, and the receptacle 112 can be formed on or associated with the movable cover 109.

One or more grooves, detents, pins, latches, or stops proximate a distal end of the movable cover 109 near the hinge 106 can lock the movable cover 109 into a deployed or opened position relative to the main body 107 (which can include a corresponding groove, detent, hole, latch or stop), to at least partially cover the needle 103.

Refer now to FIGS. 22A-22F, which show various views of the mobile cover 109. As shown in FIG. 22A, which shows a perspective view of the mobile cover 109, and in FIG. 22F, which shows a top view of the movable cover 109, a top side of the movable cover 109 includes a seat 130 bounded by two side walls 131 that abut or engage with a bottom side of the main body 109 when the movable cover 109 is in a latched or closed position, prior to removal or extraction of the needle of the needle assembly from the patient. As shown in FIGS. 22A, 22C, and 22D, a bottom side of the movable cover 109 includes a needle receptacle 132, such as a channel or cavity that is sized and adapted to receive and at least partially cover the needle 103 when the movable cover 109 is in the unlatched, deployed, open position. The needle receptacle 132 can include a deep region 134 such as a deeper channel or groove, for receiving a distal end of the needle if a Huber needle. The needle receptacle 132 and deep region 134 of the needle receptacle 132 are sized to at least partially receive the needle, and preferably to completely receive the needle so as to inhibit a clinician or anyone else from contacting the needle when the movable cover is deployed.

FIGS. 23A-23E show various views of the main body 107. The main body 107 has a proximal end 136 and a distal end 138, and includes a housing or other structure that includes or defines a channel 111 through which tubing (not shown) can be placed. In some implementations, the channel 111 extends from a proximal end 136 of the main body 107 to a point between the proximal end 136 and a distal end 138 of the main body 107, the point corresponding to an end point of the tubing from which the needle extends. The main body 107 includes one or more stabilization wings 124. In some preferred implementations, the stabilization wings 124 extend outward from opposing sides of the main body 107, and are formed as flat, planar and shaped structures that are suitable for being grasped between the fingers of a clinician. In some implementations, the stabilization wings 124 have a groove structure or texture formed into their upper and/or lower surfaces, to enable better grasping of the stabilization wings 124.

Figure 23A:
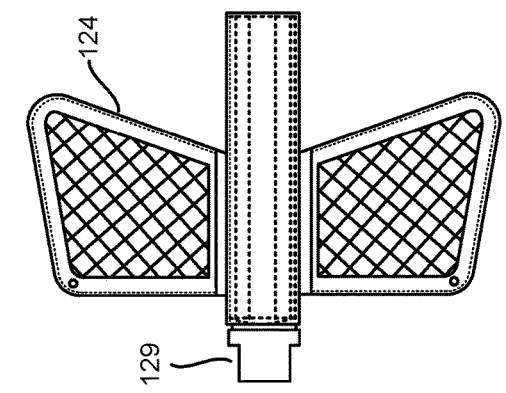
FIGS. 23A-23E show various views of a main body of the safety mechanism, to which the movable cover is pivotally latched and unlatched.
Figure 23B:
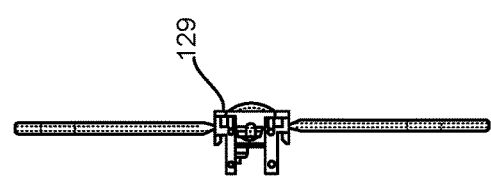
Figure 23C:
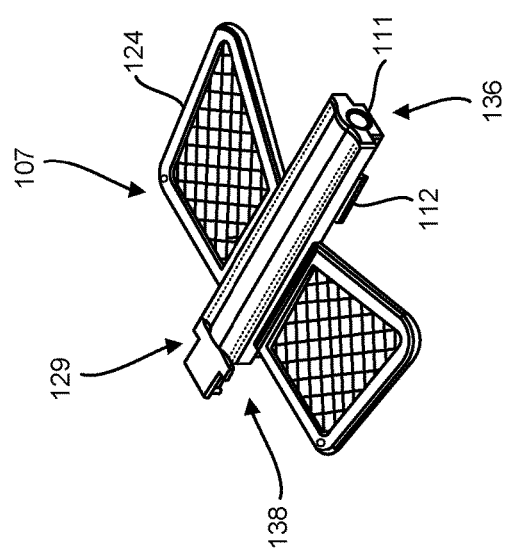
Figure 23D:
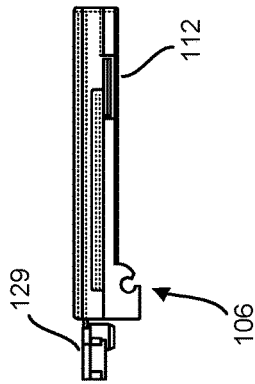

As shown in FIGS. 23B and 23D, the stabilization wings 124 are connected with the main body 107 at a flexible joint that enables the stabilization wings 124 to be bent, rotated, pivoted, flapped or otherwise moved up or down. For instance, two opposing stabilization wings 124 can be bent upward to be grasped by the clinician to control the movement, direction, insertion and extraction of the needle attached thereto. In another instance, once the needle is inserted into the skin of the patient, the two stabilization wings 124 can be bent downward toward the skin surface of the patient, or onto a patch or other retaining mechanism.

The channel 111 of the main body 107 is configured to allow the main body 107, as well as the attached movable cover 109 in a closed, retracted position, to "un-dock" or move away from the needle along the tubing shown in FIG. 21. This allows the entire safety mechanism 104, including the main body 107 and movable cover 109, to be slid or moved along the tubing 105 away from the needle 103, after the needle 103 is inserted into a point in the patient's skin. This allows the needle assembly 102 of the safety needle system 100 to have a very low profile, particularly proximate the insertion point of the needle. This can be especially important when a patient experiences weight loss, and/or the port has a tilted aspect because it may be located in an area of the chest wall that once was not "boney" but now is. Further, the stabilization wings 124, once removed from the proximity of the needle assembly 102, need not be tilted upward to compensate for any port tilting.

Figure 23E:
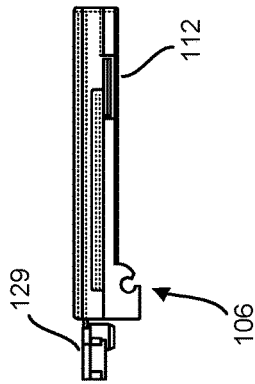

As shown in reference to FIGS. 23A, 23C, and 23E, the main body 107 further includes a securement door 129 positioned at the distal end of the main body 107. The securement door 129 can include a door that pivots downward from a point, as shown in FIG. 23E. The securement door 129 can be pivoted around and over a bend in a Huber needle, such as needle 103 shown in FIG. 21, that exists from an axis defined by the tubing 105. Further, once the securement door 129 encloses the bend of the needle 103, it locks the main body 107 in place on the tubing 105 and in a proper position for both extraction of the needle 103 from the patient, and the movable cover 109 to be activated and deployed to cover the needle 103 as explained further below.

As can be seen in FIG. 23E, the main body 107 includes receptacles that form part of a hinge 106 by which the movable cover 109 deploys or pivots from the main body 107. The receptacles can include holes, apertures, cut-outs, or the like, for receiving opposing ends of the cam lock axle 120. The receptacles can have a shape or profile to accommodate a locking or retaining member on the cam lock axle 120.

Regarding the activation and deployment of the movable cover 109 from the main body, FIGS. 24A, 24B and 24C illustrate various views of a cam lock axle 120 in accordance with some implementations. The cam lock axle 120 can be secured in the receptacles of the movable cover 109 that form part of the hinge 106, by way of flanges 142 that extend from opposing ends 140 of the cam lock axle 120, such that the cam lock axle 120 is stationary with respect to the movable cover 109 but rotating relative to the main body 107. The cam lock axle 120 will rotate until one of one or more locking flanges 122 rotate and snap into a substantially irreversible position against a tang or abutment on the main body 107. In some implementations, the locking flanges 122 originate tangential to the curve of the cam lock axle 120 and extend out and away from the axle. In other implementations, the locking flanges 122 can include a ridge that is flatter on one side than the other. In other implementations, the cam lock axle 120 can be stationary relative to the main body, and rotatable relative to the movable cover 109. Accordingly, in either implementation, once the movable cover 109 is activated and deployed, i.e. rotated from the main body 107, the cam lock axle 120 can secure the movable cover 109 in the open and covering position by locking flanges 122.

Figure 25:
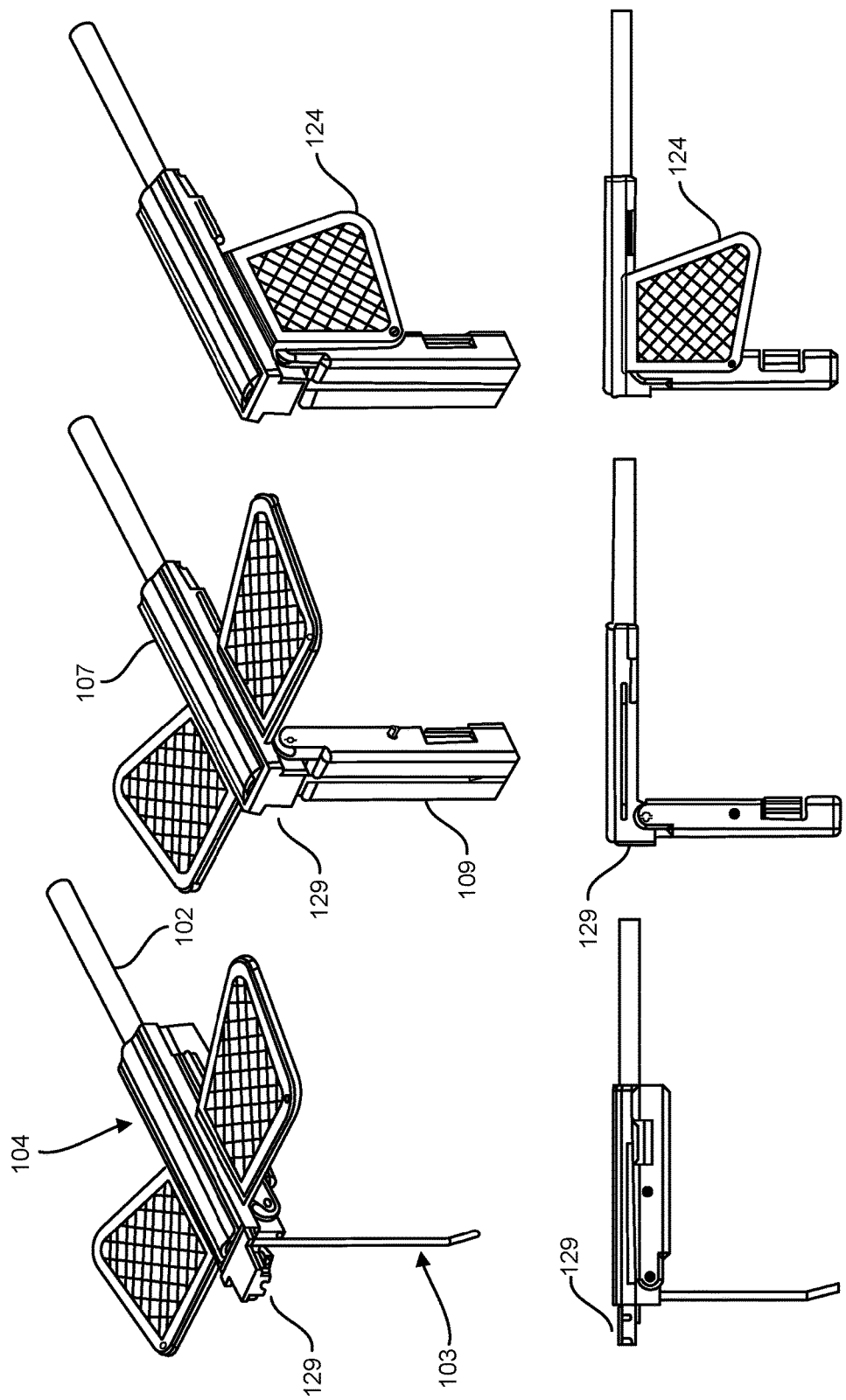
FIG. 25 illustrates various steps of use for the safety mechanism and needle assembly.

FIG. 25 shows various views of the safety needle system 100 in operation, to illustrate a method of using the safety needle system 100. At step 1, the safety needle system 100 includes a safety mechanism 104 on a needle assembly 102. As shown in step 1, the safety mechanism, which includes a main body and a movable cover as described above, are docked close to the needle 103. In some implementations, the safety mechanism can be de-docked from the needle assembly 102 and slid down tubing toward a Luer valve or other port access device.

At step 2, the movable cover 109 is activated and deployed in an open, locked position to cover the needle 103 of the needle assembly 102. As shown, the needle 103 fits into a channel in the moveable cover 109 to an extent that the needle 103 is not accessible by a clinician or other person. Upon completion of step 2, the movable cover 109 is locked, irreversibly, in the open position to cover the needle 103. For further protection and as an extra measure of safety, a containment device can be formed as shown in step 3. The stabilization wings 124 of the main body 107 can be folded down to lock into position with the movable cover 109 via locking mechanism. The locking mechanism can include pins and corresponding holes or apertures, but may also include channels and corresponding flanges, tongue-and-groove locking members, hook-and-loop systems, snaps, screws, pins, or the like. In this manner, the safety needle system 100 presents as a strong containment device that can be disposed of without fear of deactivating the movable cover 109, and able to withstand rough handling by any hospital or janitorial staff.

Figure 26A:
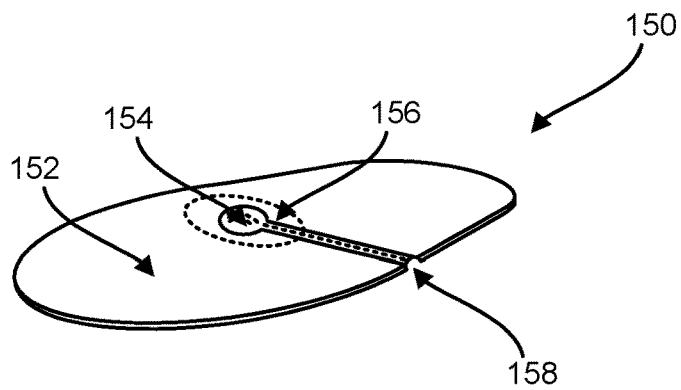
FIGS. 26A-26C illustrate a securement device and its use, in accordance with implementations described herein.
Figure 26B:
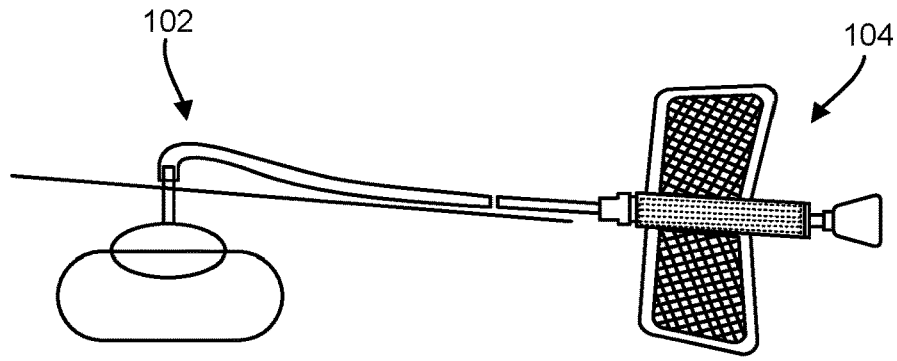
Figure 26C:
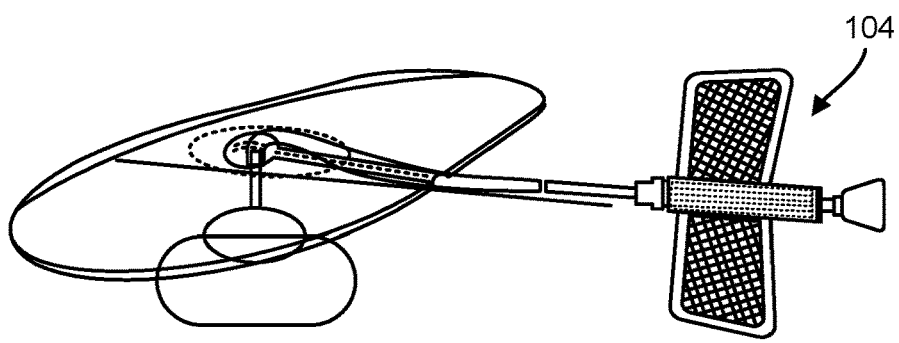

FIGS. 26A-26C illustrates a securement device 150 for an un-docked a needle assembly 102 from the safety mechanism 104, or conversely an un-docked safety mechanism 104 from the needle assembly 102. The securement device 150 includes a substantially planar foam pad 152, which can be formed of breathable ECG or medical cloth. The foam pad 152 may also include an adhesive on a bottom (patient skin side) of the foam pad 152. A dome 154 is provided to accommodate needle protrusion. The dome 154 can be oblong or rounded, and be formed of a rigid or semi-rigid material such as plastic or nylon. The securement device 150 can further include an anti-microbial layer or substrate, that is substantially underneath and/or surrounding the dome 154 to surround the entry point of the needle on the patient. The securement device 150 can also include a tubing capture and retention channel 158 from the dome 154 and directed outward to a periphery of the securement device 150.

In use, as illustrated in FIGS. 26A and 26B, the securement device 150 is placed on the skin with the paper barriers separating the adhesive from contact with the skin or the fingers of the care giver. The tubing is guided into the tubing retention channel 158. The securement device 150 may be slid along the tubing using the tubing capture and retention channel 158 as an alignment to guide the tubing into a position where the area with no adhesive can be covered by a clear film, which will provide an area for visualization of the needle interface with the skin for purposes of correct positioning as well signs of infection in subsequent days.

By grasping the tubing with the securement device 150, any strain on the tubing will be managed by the connection of the tubing to the channel in the securement device 150 and thus transferred to the adhesive interface with the skin. The downward force on the needle by the clear area membrane will maintain the needle in the appropriate position in the skin and thus the port.

Although a few embodiments have been described in detail above, other modifications are possible. Other embodiments and implementations may be within the scope of the following claims.

The invention claimed is:

1. A safety mechanism for a Huber needle assembly having a tubing and a needle extending from a distal end of the tubing, the safety mechanism comprising:

a main body defining a channel to at least partially encompass the tubing and having a distal end, a proximal end, opposing side walls, and a securement door coupled at the distal end of the main body, the securement door being pivotable between a closed position to dock the main body to the needle and an open position enabling the main body to be de-docked from the needle and slid along the tubing for being positioned between the needle of the Huber needle assembly and an inlet of the tubing, the main body further having a first hinge mechanism near the distal end of the main body and a first latching mechanism toward the proximal end of the main body; and a movable cover having a needle receptacle, a second hinge mechanism connected with the first hinge mechanism of the main body by a cam lock axle, and a biasing member for pivoting the movable cover about the first and second hinge mechanisms relative to the main body, the movable cover further having a second latching mechanism to latch with the first latching mechanism in a closed position to retract the movable cover to engage with a bottom side of the main body, the movable cover further having a release mechanism to release latching between the first and second latching mechanisms to allow the pivoting of the movable cover about the first and second hinge mechanisms such that the needle receptacle of the movable cover at least partially receives the needle of the Huber needle assembly in an open position.

2. The apparatus in accordance with claim 1, wherein the main body further includes one or more stabilization wings extending from the main body, the one or more stabilization wings being pivotable about an axis that is parallel to the channel of the main body.

3. The apparatus in accordance with claim 2, further comprising:
a first securement mechanism on the movable cover; and
a second securement mechanism on at least one of the one or more stabilization wings, the second securement mechanism for coupling with the first securement mechanism when the movable cover is in the open position to secure the movable cover to at least partially cover the needle.

4. The apparatus in accordance with claim 3, wherein the first securement mechanism includes a pin, and wherein the second securement mechanism includes a hole for receiving the pin when the movable cover is in the open position.

5. The apparatus in accordance with claim 3, wherein the first securement mechanism includes a first latch, and wherein the second securement mechanism includes a second latch for latching with the first latch when the movable cover is in the open position.

6. The safety mechanism in accordance with claim 1, wherein the cam lock axle includes at least one locking flange that engages a tang protruding from the main body.

7. A safety mechanism for a Huber needle assembly having tubing and a needle extending from a distal end of the tubing, the safety mechanism comprising:
a main body that is elongated and having a distal end, a proximal end, opposing side walls, and a securement door at the distal end of the main body, the main body defining a channel to at least partially encompass the tubing, the securement door being pivotable between a closed position to dock the main body to the needle and an open position enabling the main body to be slid away from the needle and positioned along the tubing between the needle of the Huber needle assembly and an inlet of the tubing, the main body further having a first hinge mechanism near the distal end of the main body and a first latching mechanism toward the proximal end of the main body; and
a movable cover having a needle receptacle, a second hinge mechanism connected with the first hinge mechanism of the main body by a cam lock axle, and a biasing member for pivoting the movable cover about the first and second hinge mechanisms relative to the main body, the movable cover further having a second latching mechanism to latch with the first latching mechanism in a closed position to retract the movable cover to engage with a bottom side of the main body, the movable cover further having a release mechanism to release latching between the first and second latching mechanisms to allow the pivoting of the movable cover about the first and second hinge mechanisms such that the needle receptacle of the movable cover at least partially receives the needle of the Huber needle assembly in an open position.

8. The safety mechanism in accordance with claim 7, wherein the cam lock axle includes at least one locking flange that engages a tang protruding from the main body.

9. The safety mechanism in accordance with claim 7, wherein the main body includes a pair of stabilization wings extending from the opposing side walls, each of the pair of stabilization wings being independently movable upward to be grasped by a user.

10. The safety mechanism in accordance with claim 9, wherein the pair of stabilization wings are movable downward to lock with the movable cover when the moveable cover is in locked in the open position.

11. A passive safety Huber needle system comprising:
a needle assembly comprising tubing and a needle extending from a distal end of the tubing; and
a safety mechanism associated with the needle assembly, the safety mechanism comprising:
a main body having a channel at least partially encompassing the tubing and a distal end for being positioned proximate the needle of the assembly, the main body further having a securement door at the distal end of the main body that is pivotable between a closed position to secure the main body proximate the needle and an open position enabling the main body to be slid away from the needle, the main body further having a first hinge mechanism near a distal end of the channel and a first latching mechanism toward a proximal end of the channel; and
a movable cover having needle receptacle, a second hinge mechanism connected with the first hinge mechanism of the main body, and a biasing member for pivoting movable cover about the first and second hinge mechanisms relative to the main body, the movable cover further having a second latching mechanism to latch with the first latching mechanism in a closed position to retract the movable cover to engage with a bottom side of the main body, the movable cover further having a release mechanism to release latching between the first and second latching mechanisms to allow pivoting of the movable cover about the first and second hinge mechanisms such that the needle receptacle of the movable cover at least partially receives the needle of the needle assembly in an open position.

12. The safety mechanism in accordance with claim 11, wherein the movable cover includes a cam lock axle that includes at least one locking flange that engages a tang protruding from the main body.

13. The safety mechanism in accordance with claim 11, wherein the main body includes a pair of stabilization wings extending from the opposing side walls, each of the pair of stabilization wings being independently movable upward to be grasped by a user.

14. The safety mechanism in accordance with claim 13, wherein the pair of stabilization wings are movable downward to lock with the movable cover when the moveable cover is in locked in the open position.

15. A safety mechanism for a Huber needle assembly having tubing and a needle extending from a distal end of the tubing, the safety mechanism comprising:
a main body having a channel, the channel having a proximal end at least partially encompassing the tubing and a distal end for being positioned proximate the needle of the Huber needle assembly, the main body further having a securement door at the distal end of the main body that is pivotable between a closed position to secure the main body proximate the needle and an open position enabling the main body to be slid away from the needle, the main body further having a first hinge mechanism near the distal end of the channel and a first latching mechanism toward the proximal end of the channel; and
a movable cover having needle receptacle, a second hinge mechanism connected with the first hinge mechanism of the main body, and a biasing member for pivoting movable cover about the first and second hinge mechanisms relative to the main body, the movable cover further having a second latching mechanism to latch with the first latching mechanism in a closed position to retract the movable cover to engage with a bottom side of the main body, the movable cover further having a release mechanism to release latching between the first and second latching mechanisms to allow the pivoting of the movable cover about the first and second hinge mechanisms such that the needle receptacle of the movable cover at least partially receives the needle of the needle assembly in an open position.

16. The safety mechanism in accordance with claim 15, wherein the movable cover includes a cam lock axle that includes at least one locking flange that engages a tang protruding from the main body.

17. The safety mechanism in accordance with claim 15, wherein the main body includes a pair of stabilization wings extending from the opposing side walls, each of the pair of stabilization wings being independently movable upward to be grasped by a user.

18. The safety mechanism in accordance with claim 17, wherein the pair of stabilization wings are movable downward to lock with the movable cover when the moveable cover is in locked in the open position.

19. The safety mechanism in accordance with claim 18, wherein the stabilization wings include a first locking mechanism to lock with a corresponding second locking mechanism on the movable cover.

* * * * *